(12) United States Patent
Cassily

(10) Patent No.: US 6,719,690 B1
(45) Date of Patent: Apr. 13, 2004

(54) NEUROLOGICAL CONFLICT DIAGNOSTIC METHOD AND APPARATUS

(75) Inventor: James F. Cassily, Grand Rapids, MI (US)

(73) Assignee: Synaptec, L.L.C., Weston, FL (US)

(*) Notice: Subject to any disclaimer, the term of this patent is extended or adjusted under 35 U.S.C. 154(b) by 0 days.

(21) Appl. No.: 10/048,505
(22) PCT Filed: Aug. 11, 2000
(86) PCT No.: PCT/US00/21855

§ 371 (c)(1),
(2), (4) Date: Jan. 30, 2002

(87) PCT Pub. No.: WO01/12058

PCT Pub. Date: Feb. 22, 2001

Related U.S. Application Data

(60) Provisional application No. 60/219,321, filed on Aug. 13, 1999, and provisional application No. 60/229,361, filed on Aug. 13, 1999.

(51) Int. Cl.[7] .................................................. A61B 5/00
(52) U.S. Cl. ........................ 600/300; 434/258; 434/236
(58) Field of Search ................................ 600/300, 301; 705/2, 3; 128/920–925; 434/116, 258, 236

(56) References Cited

U.S. PATENT DOCUMENTS

| 5,511,982 | A |   | 4/1996  | Pigache et al. |
| 5,529,498 | A |   | 6/1996  | Cassily et al. |
| 5,687,716 | A | * | 11/1997 | Kaufmann et al. ......... 600/300 |
| 5,743,744 | A |   | 4/1998  | Cassily et al. |
| 5,888,074 | A |   | 3/1999  | Staplin et al. |
| 5,913,310 | A |   | 6/1999  | Brown |
| 6,113,538 | A |   | 9/2000  | Bowles et al. |
| 6,126,596 | A | * | 10/2000 | Freedman .................... 600/300 |
| 6,212,519 | B1| * | 4/2001  | Segal ............................ 705/2 |

OTHER PUBLICATIONS

Paper entitled "Improving Student Motor Integration by Use of an Interactive Metronome™," presented at the Annual Meeting of the American Educational Research Assoc., Mar. 24, 1997, by Paul M. Stemmer, Jr.

Clinical Guide entitled "T.O.V.A.® Test of Variables of Attention," published in 1996, by Lawrence Greenberg.

* cited by examiner

Primary Examiner—Eric F. Winakur
Assistant Examiner—David J. McCrosky
(74) Attorney, Agent, or Firm—Van Dyke, Gardner, Linn & Burkhart, LLP

(57) ABSTRACT

A timing assessment tool (12) is provided that is manipulatable by a user (8) in response to the user's expected occurrence of a rhythmic reference signal. The timing assessment tool derives a rhythmic assessment from a pattern of user responses to the user's expected occurrence of the rhythmic reference signal. An analyzer (14), which may include a database (30), is provided to respond to the rhythmic assessment to indicate a diagnosis and/or corrective intervention,

62 Claims, 10 Drawing Sheets

NEUROLOGICAL CONFLICT DIAGNOSTIC METHOD AND APPARATUS

CROSS-REFERENCE TO RELATED APPLICATIONS

This application claims priority from provisional patent application Serial No. 60/219,321 filed on Aug. 13, 1999, and provisional patent application Serial No. 60/229,361 filed on Aug. 13, 1999, the disclosures of which are incorporated herein in their entirety by reference.

BACKGROUND OF THE INVENTION

This invention relates to a method and apparatus for diagnosing neurological conflicts in persons. The invention is especially adapted to diagnosing learning disabilities, but has application in diagnosing other neurological conflicts. The invention may also be used to prescribe corrective interventions for neurological conflicts.

Diagnostic criteria for various learning related disorders are contained in the volume of DSM IV diagnostic codes of the American Psychiatric Association. One such disorder is Attention Deficit Hyperactivity Disorder (ADHD). Questions are raised whether ADHD constitutes an actual syndrome in view of the variability of symptoms across settings and parameters which may affect this variability. Barkley, R. A., "A Critique of Current Diagnostic Criteria for Attention Deficit Hyperactive Disorder: Clinical and Research Implications," *J. Dev. Behav. Pediatr.*, 11(6): 343–52 (1990). ADHD is often present with other disorders, such as Oppositional Defiant Disorder (ODD). Conduct Disorder (CD), Dyslexia, Tourette Syndrome (TS), and the like. It is also known that ADHD may result from one or more disorders. For example, there is an excess prevalence of premorbid ADHD among children who are present with moderate and severe Closed Head Injury (CHI). Gerring, J. P., Brady, K. D. et al., "Premorbid Prevalence of ADHD and Development of Secondary ADHD After Closed Head Injury," *J. Am. Acad. Child. Adolesc. Psychiatrv*, 37(6): 647–54 (1998). Children born to mothers who had abused alcohol throughout pregnancy also produces ADHD along with other intellectual problems. Aronson, M. B., Hagberg et al., "Attention Deficits and Autistic Spectrum Problems in Children Exposed to Alcohol During Gestation: A Follow-up Study," *Dev. Med. Child Neurol.*, 39(9): 583–7 (1997).

It is imperative that a child with a neurological disorder which may lead to a learning disability be diagnosed and corrective intervention be prescribed as early as possible. It is now known that the best time to learn foreign languages, mathematics, music, and other subjects is between the ages of 1 and about 12. Kotulak, R., "Inside the Brain," Andrews, McMeel Publishing, 1997. Therefore, the failure to promptly intervene may result in the therapy occurring beyond the prime developmental years for the brain.

Because of the interrelated nature and multiple potential causes of various learning disorders, present therapeutic techniques are designed to deal with surface behavior; namely, the symptoms of the underlying causes. It is widely accepted that current diagnostic techniques are incapable of sorting out the various disorders and their underlying causes. As a result, the prescription of corrective interventions is based upon trial and error which is inadequate given the short time span of the peak developmental period of the brain.

An important relationship between attention and aspects of motor regulation including inhibition, speed, rhythm, coordination and overflow has been postulated by several investigators (Barkley, R. A.; DuPaul, G. J. et al. (1990); Denckla, M. B.; Rudel, R. et al. (1985); and Piek, J. P. et al. (1999)). Gillberg, C. (1988) has described a group of children with deficits in attention, motor control, and perception termed "DAMP syndrome" in a recent study, and found considerable overlap between attention deficits and motor clumsiness (Kadesjo, B. and Gillberg, C. (1998)). Piek, J. P. (1999) has recently demonstrated that severity of inattentive symptomatology in ADHD boys is a significant predicator of motor coordination difficulties. However, there has been no practical tool proposed to assist in the diagnosis of disorders on the basis of measuring the timing of the individual. Physiological tests are subjective and, therefore, depend upon the skill and condition of the test taker at any particular time. Some tests are capable of directly measuring neurological disorders, such as MRI examinations. However, such MRI examinations are intrusive in that they require that a particular dye be injected into the bloodstream as part of the examination process.

SUMMARY OF THE INVENTION

A neurological conflict diagnostic apparatus according to the invention includes a timing assessment tool. The timing assessment tool is manipulatable by a user and develops a timing score. A processor processes the timing score to a diagnosis and/or corrective intervention, or therapy. This may be accomplished by the processor applying the score from the timing assessment tool to a database and retrieving a diagnosis, a therapeutic intervention, or both from the database.

The use of a timing assessment tool eliminates the subjectivity that is present in other clinical rated timing assessments. Furthermore, because the timing assessment tool is manipulated by a user, the timing assessment tool is capable of assessing neurological functions which correlate with outward symptoms rather than measuring outward symptoms alone. Because the database relates timing scores with diagnosis and therapeutic interventions with various diagnoses, the inclusion of a large sampling of users in a database and performing of statistical analysis on the population allows a direct correlation between timing scores and therapeutic interventions without the necessity for establishing a known diagnosis.

According to another aspect of the invention, a diagnostic apparatus includes at least one user operable trigger, a control, and a database. The control generates a reference signal having occurrences separated by a predetermined time interval and determines a temporal relationship between user manipulation of the trigger and occurrences of the reference signal. A database includes a plurality of such temporal relationships and a diagnosis, a therapeutic intervention, or both for the temporal relationships. Preferably, the diagnosis apparatus includes a plurality of triggers that are operable by different user limbs. The timing assessment tool may be used to develop a timing score based upon a comparison of user manipulation of the different triggers. The reference signal may be either a non-speech tone or a series of different speech phonetic sounds in order to diagnose different disorders.

A method of determining a therapeutic intervention for a person having a neurological conflict according to another aspect of the invention includes providing a database of therapeutic interventions and timing parameters. The method further includes objectively measuring the timing parameter of the person and applying the measured timing parameter to the database and retrieving at least a therapeutic intervention from the database. The objectively measured timing of the person may include measuring any one of the person's response time, response variability, break-in response sequence, out-of-phase responses, interactive responses, early responses, late responses, and any combination of such responses.

The present invention may obviate the need for conventional psychological testing, with its present subjective evaluations, and the necessity for identifying any one particular diagnosis. Instead, the present invention provides the capability for directly correlating timing parameters indicative of neurological conflict in order to establish a therapeutic intervention specific to the neurological conflict.

The present invention is intended to provide a tool for diagnosing and prescribing therapeutic intervention especially for learning disabilities but may be useful for other neurological conflicts such as Parkinson's disease, Alzheimer's disease, and the like. The invention is especially useful in improving the attention, motor and perceptual motor functioning, cognitive and academic performance, and control of aggression in children with significant attentional problems.

These and other objects, advantages, and features of this invention will become apparent upon review of the following specification in conjunction with the drawings.

DESCRIPTION OF THE PREFERRED EMBODIMENT

Referring now specifically to the drawings, and the illustrative embodiments depicted therein, a conflict diagnostic method and apparatus 10 includes a timing assessment tool 12 and analyzer, or processor, 14. The analyzer 14 receives a timing score illustrated at 16 from timing assessment tool 12 and produces an indication at 18 which may be a diagnostic indication, a therapeutic intervention indication, or both diagnostic and therapeutic indications. It should be understood that timing assessment tool 12 and analyzer 14 may be separate units or combined together in a single unit.

Figure 1:
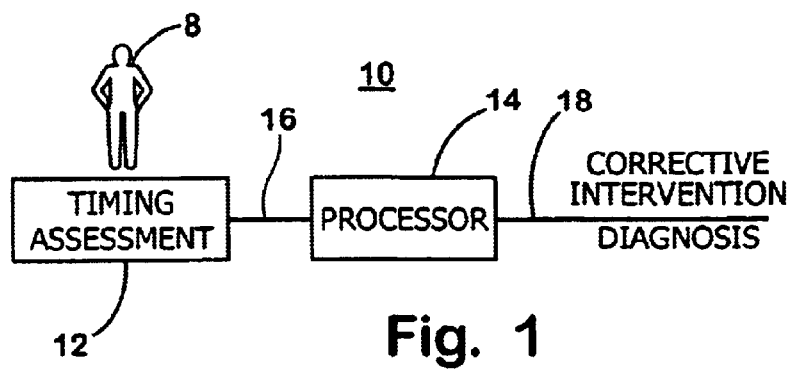
FIG. 1 is a block diagram of a neurological conflict diagnostic method and apparatus according to the invention.
Figure 2:
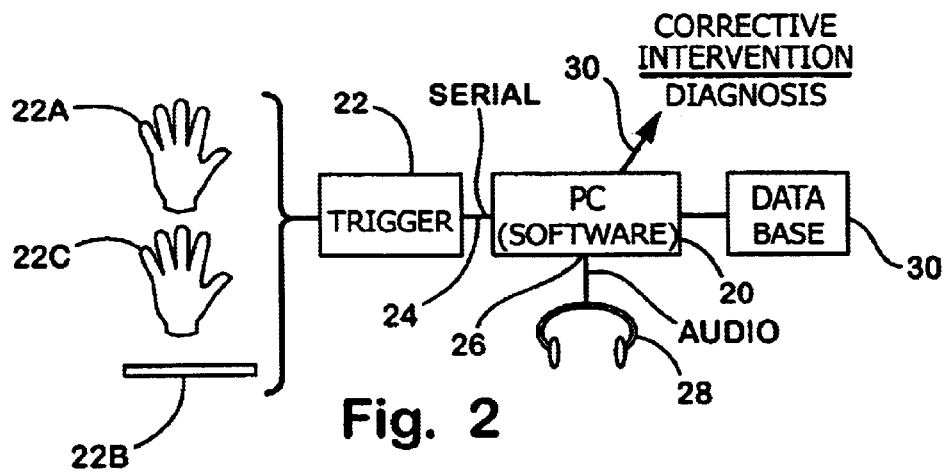
FIG. 2 is a detailed block diagram of a neurological conflict diagnostic apparatus.

In the illustrated embodiment, timing assessment tool 12 is preferably a neuro-motor coordination measuring and enhancing apparatus of the type disclosed in commonly assigned U.S. Pat. Nos. 5,529,498 and 5,743,744 entitled METHOD AND APPARATUS FOR MEASURING AND ENHANCING NEURO-MOTOR COORDINATION, the disclosures of which are hereby incorporated herein by reference. In one illustrated embodiment, timing assessment tool 12 includes a personal computer 20 which is preferably an IBM compatible personal computer with a 266 or higher megahertz Pentium processor with a Windows '98 operating system, 64 megabytes of RAM, and 100 megabytes of free space on the main hard drive (FIG. 2). Other operating systems, such as Apple or Linux, may also be used. Computer 20 may be a laptop computer for portability purposes. The timing assessment tool may also be a dedicated hardware platform thereby allowing the tool to be carried by the user's body. In the illustrated embodiment, personal computer 20 is loaded with Interactive Metronome® ProVersion 4.0 Software. A trigger 22 is connected through a serial port 24 of computer 20. Computer 20 preferably includes a 100 percent Sound Blaster compatible stereo sound card producing an output 26 selected to a pair of stereo headphones 28 or other multiple speaker system. However, customdesigned sound-generating circuits may be used. Trigger 22 may include one or more hand triggers 22A, 22C, and a foot trigger 22B. Hand triggers 22A, 22C may be utilized on opposite hands, and foot trigger 22B may be struck by either foot with either the toe or the heel. The triggers 22 are utilized to provide a user input to computer 20. A database 30 which may reside on a separate computer or on computer 20 provides relationship between timing scores produced by timing assessment tool 12 and diagnosis and/or therapy interventions in a manner that will be explained in more detail below. Computer 20 produces an output 30 which is a diagnosis and/or a corrective intervention for the user 8 of the timing assessment tool.

In operation, a person to be tested, which preferably is a child of preschool or early grade school age, is fitted with one or more triggers 22. A reference signal is generated by computer. The reference signal may be provided to the user. The user is instructed to actuate the trigger when the user expects the next reference signal to be generated. Preferably, computer 20 does not produce a guidance signal on headphones 28 that indicates to the user the relationship between the user's response on the trigger 22 and the reference signal. As such, the test subject may only hear the reference sound, which is periodic. In one embodiment of the invention, the reference beat is a musical tone, such as a cowbell, but, as will be set forth in detail below, may be other sounds as well. It should be understood that the present invention also comprehends the use of guidance signals, which may be aural or visual. Alternatively, the user may be provided only guidance signals and no reference signal.

The user is instructed to perform various responses with each of the triggers 22a on each of the hands and alternating from hand-to-hand as well as foot trigger 22b with each of the feet and alternating from foot-to-foot. Computer 20 evaluates the responses of the user in order to identify various patterns of responses. These may include, but are not limited to, the following: a) Consistency of response; b) timing; c) score, d) variability of response; e) average response time; f) front of beat or back of beat; g) missed responses; i.e., break in sequence; h) out-of-phase responses; i.e., responding to the wrong reference signal; i) erratic responses; j) multiple hits between beats, and the like. Computer 20 then attempts to match the pattern produced by the user to a series of parameters stored in database 30 and utilizes conventional data fitting software to determine the best fit between the pattern of the user and the pattern stored in database 30 Computer 20 then retrieves the diagnosis and/or corrective intervention from database 30 corresponding to the selected pattern and displays the diagnosis, a corrective intervention, or both the diagnosis and a corrective intervention at 32 to the machine operator. The user inputs that may be performed on trigger 22 include the following: a) Clapping both hands together; b) tapping preferred hand; c) tapping non-preferred hand; d) alternating toe taps; e) taps with the preferred toe; f) taps with the non-preferred toe; g) alternating heel taps; h) taps with the preferred heel; i) taps with the non-preferred heel; j) alternating preferred hand/non-preferred toe taps; k) alternating non-preferred hand/preferred toe taps; I) balance on the preferred foot and tap with the non-preferred toe; and m) balance on the non-preferred foot and tap with the preferred toe.

Another useful assessment tool may be to measure impacts of the user on the triggers, known as ballistics. This could be assessed by the test administrator monitoring the movements of the user, or by the timing assessment tool 12. This could be performed by measuring the pressure level and duration of the hits.

Timing assessment tool 12 may generate random distraction sounds in addition to the reference sounds. The reference sounds may be fixed or may be developed in response to the performance of the user. In addition to providing additional information on the distractibility of the user, the distraction sounds can be used to mitigate a retest bias resulting from multiple performance of the test by a user.

Figure 3:
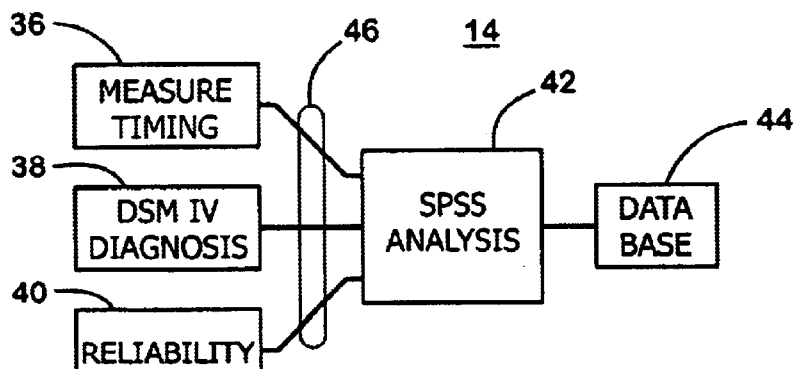
FIG. 3 is a block diagram of a method of developing a database useful with the invention.

Database 30 is developed according to a data gathering method 34 (FIG. 3). A multiplicity of users are tested utilizing timing assessment tool 12 at 36. The testing is preferably a long-form pretest that is performed at the beginning of a training session on the device disclosed in the '744 patent and in the commonly assigned application and at the end of such training session. The test may be performed in combination with a training session or may be performed without such training. The test is preferably conducted without guide sounds provided to the user. Along with the measured timing of the individual, a diagnosis for the individual is entered utilizing standard diagnostic codes, such as the Diagnostic & Statistical Manual DSM IV diagnostic codes provided by the American Psychiatric Association as well as other diagnostic codes known in the field. The diagnostic code indicates any diagnostic made for that individual, such as Attention Deficit Hyperactivity Disorder (ADHD), Oppositional Defiant Disorder (ODD), Dyslexia, NVLD, tics, such as Tourette Syndrome (TS), Closed Head Injury (CHI), language disorder, Developmental Coordination Disorder (DCD), Deficit and Attention Motor Control and Perception (DAMP), Language Impaired (LI), Aggressive-Hyperactive-Impulsive-Inattentive behavior (AHII), autism, Parkinson's disease, claustrophobia, and the like. Along with entering the diagnosis at 38, a diagnosis reliability indication is entered at 40. The reliability indication 40 indicates the reliability of the person making the diagnosis. For example, if the diagnosis is made on the basis of parental observation, then it may have a particular reliability weight. If the diagnosis is made in a clinical setting by a trained psychiatric professional, it may have a different weight. Upon collecting a statistically significant sample of diagnosis and measurement patterns entered in this fashion, a statistical analysis such as a SPSS statistic analysis is performed on the data at 42 and a database is developed at 44. The statistical analysis is to examine among tests performed by users to determine if particular patterns correlate with particular diagnoses and interventions. Other statistical tools, such as SAS, Excel, and the like, may be used. Data may be entered at 46 utilizing any conventional technique, such as over the Internet. Confidentiality may be preserved by assigning a random number to each subject in order to avoid identifying the individual with a particular disorder. An example of a test data sheet is attached hereto as Appendix A.

Database 44 may include three tables: (a) background table for users; (b) summary of performance by users on the time test; and (c) raw data of individual hits by users to the reference sounds. The inclusion of the third table allows researchers to perform additional statistical analyses on the data beyond that possible from the first two tables. Preferably, all test results entered into the database are encrypted, such as by utilizing parity numbers. This provides a mechanism for detecting corruption of the database, such as by researchers tampering with test results.

An additional test that may be incorporated into a timing score may be to measure a user's natural tempo. This may be done by instructing the user to tap steadily with a particular trigger, such as both hands together at any tempo the user is comfortable with. Timing assessment tool 12 analyzes the occurrences and gives a numeric value which represents the natural tempo of that user without any reference being used. This additional diagnostic number may provide additional data that could be applied to the database to find correlation to known diagnosed populations with particular disorders or disabilities.

In addition to musical tone or percussive tone reference, the invention further contemplates utilizing phonetic sounds as the reference in order to assist in diagnosing phonetic learning problems. These may include the T sound, the S sound, the Th sound, the Ch sound, and the like for a reference. While the full understanding of the manner in which neurological conflict diagnostic apparatus and corresponding methods operate is being developed, it is believed that the basis of operation is as follows. Children who perform well on the apparatus disclosed in the '744 patent have been shown to be able to focus on a particular task. Focus is the foundation of mental control. When the brain focuses, it recruits neuro-multi-tasking functions to operate as a unit and maintains that unit throughout the task. As the user performs the various subtests using the timing assessment tool, certain parts of the brain are involved in the operation in the different parts of the body; namely, the limbs. Timing assessment tool 12 measures the brain's ability to recruit and maintain neuro connections during specific elementary motor tasks that are related to the certain functions within the brain.

Disorders, or failures, of the brain produce particular symptoms which are behavioral in nature. The symptoms represent a failure of the person to learn in some manner. Overlap between portions of the brain involved in controlling the limbs operating the triggers of the timing assessment tool, because of the variation in the manner in which the limbs are operated, causes some overlap with the portions of the brain having the disorders which produce the symptoms. It is not necessary to identify the portion of the brain causing the disorder. It is only necessary to correlate the pattern in the assessment performed on the timing assessment tool with the same pattern produced in other individuals and to identify the diagnosis of the other individuals. In this manner, the neurological conflict diagnosis apparatus 10 measures deficiencies in certain multi-tasking functions over other multi-tasking functions which will correlate to outward symptoms, such as dyslexia, ADHD, cerebral palsy, autism, Parkinson's disease, and the like. Because certain parts of the brain are involved in both the outward symptoms and the pattern of testing, the diagnosis and, hence, the correlational diagnosis and/or corrective intervention will be revealed by the pattern produced by the testing.

Figure 4:
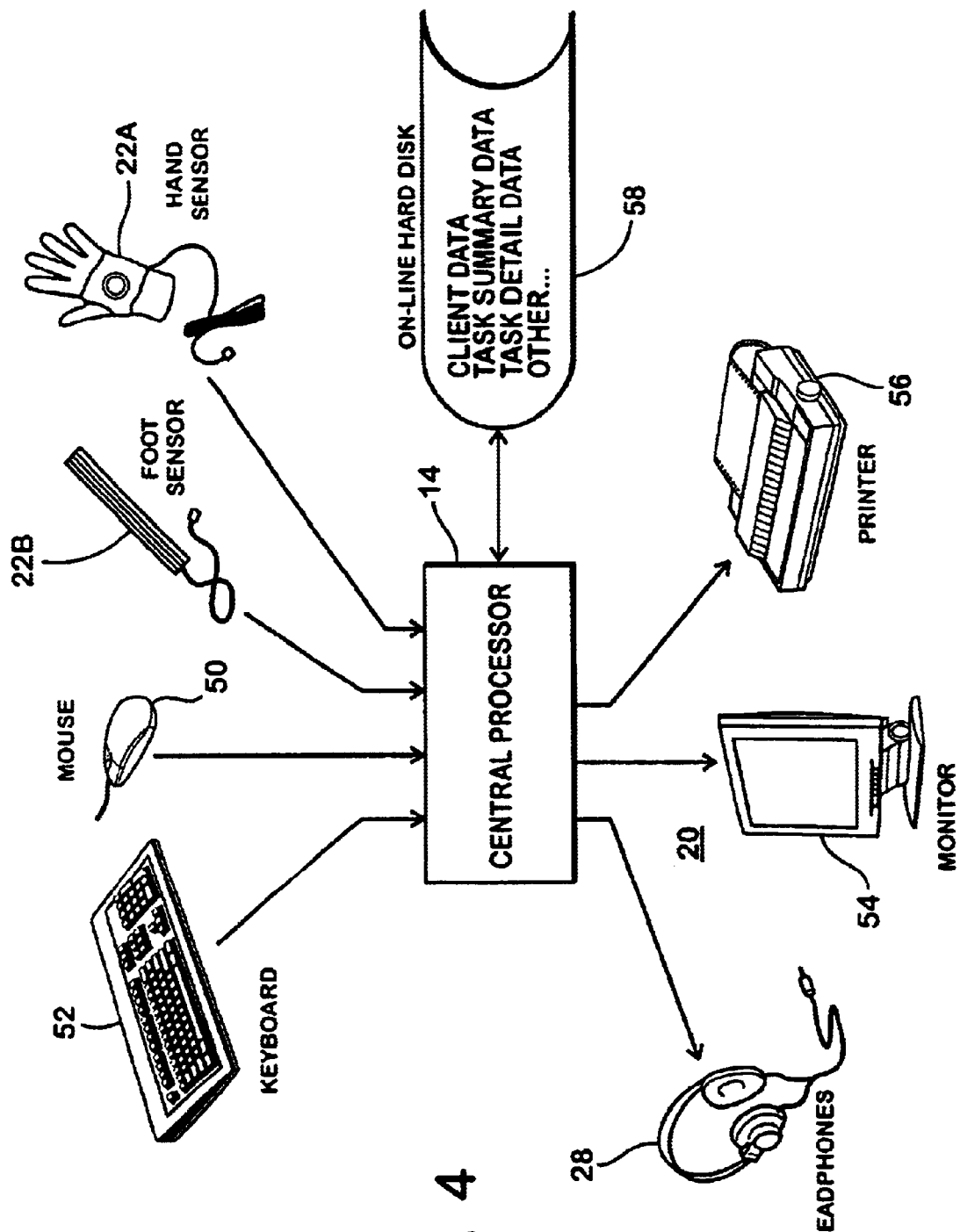
FIG. 4 is a somewhat more detailed view of the apparatus in FIG. 2.
Figure 5:
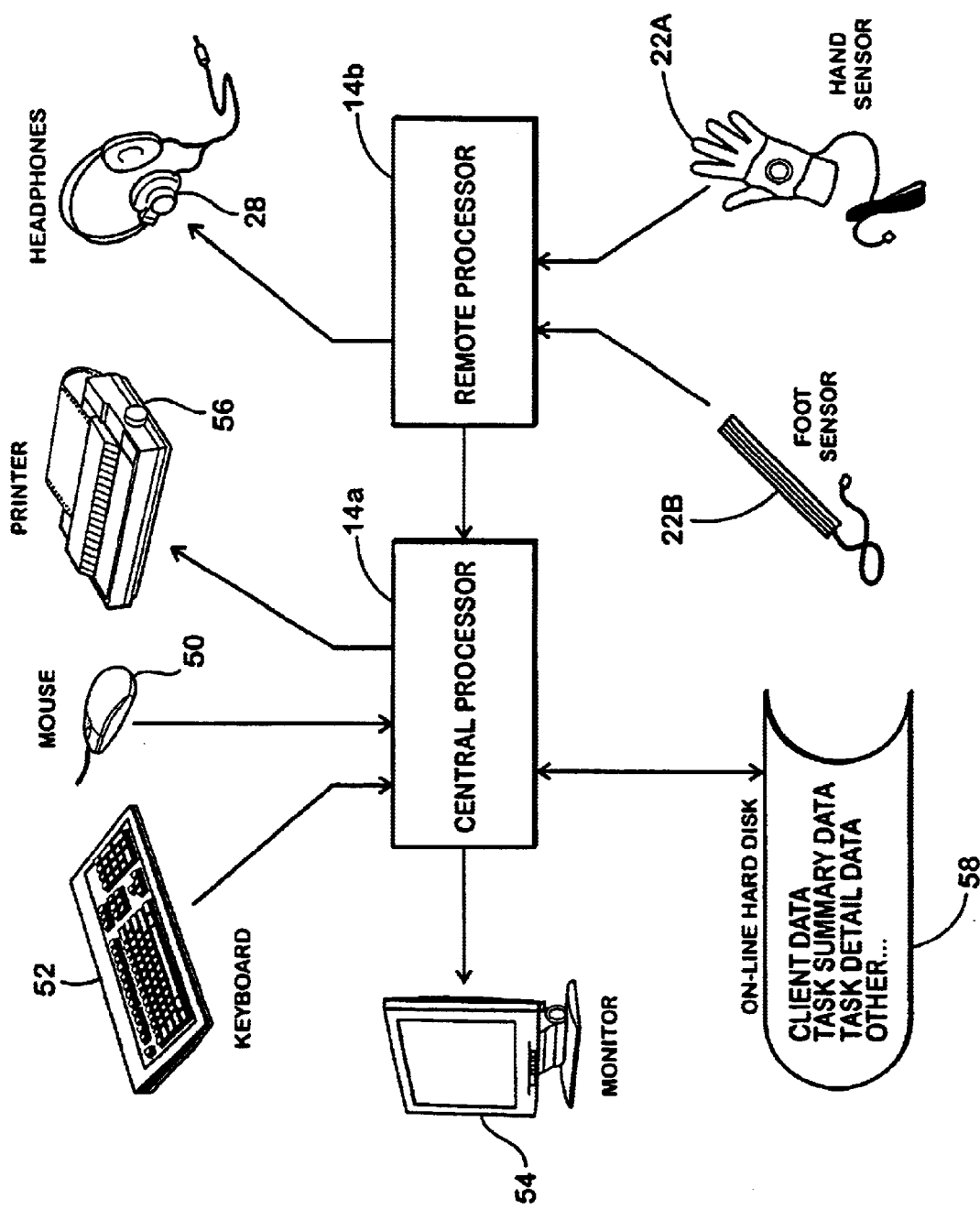
FIG. 5 is the same view as FIG. 4 of an alternative embodiment.
Figure 6:
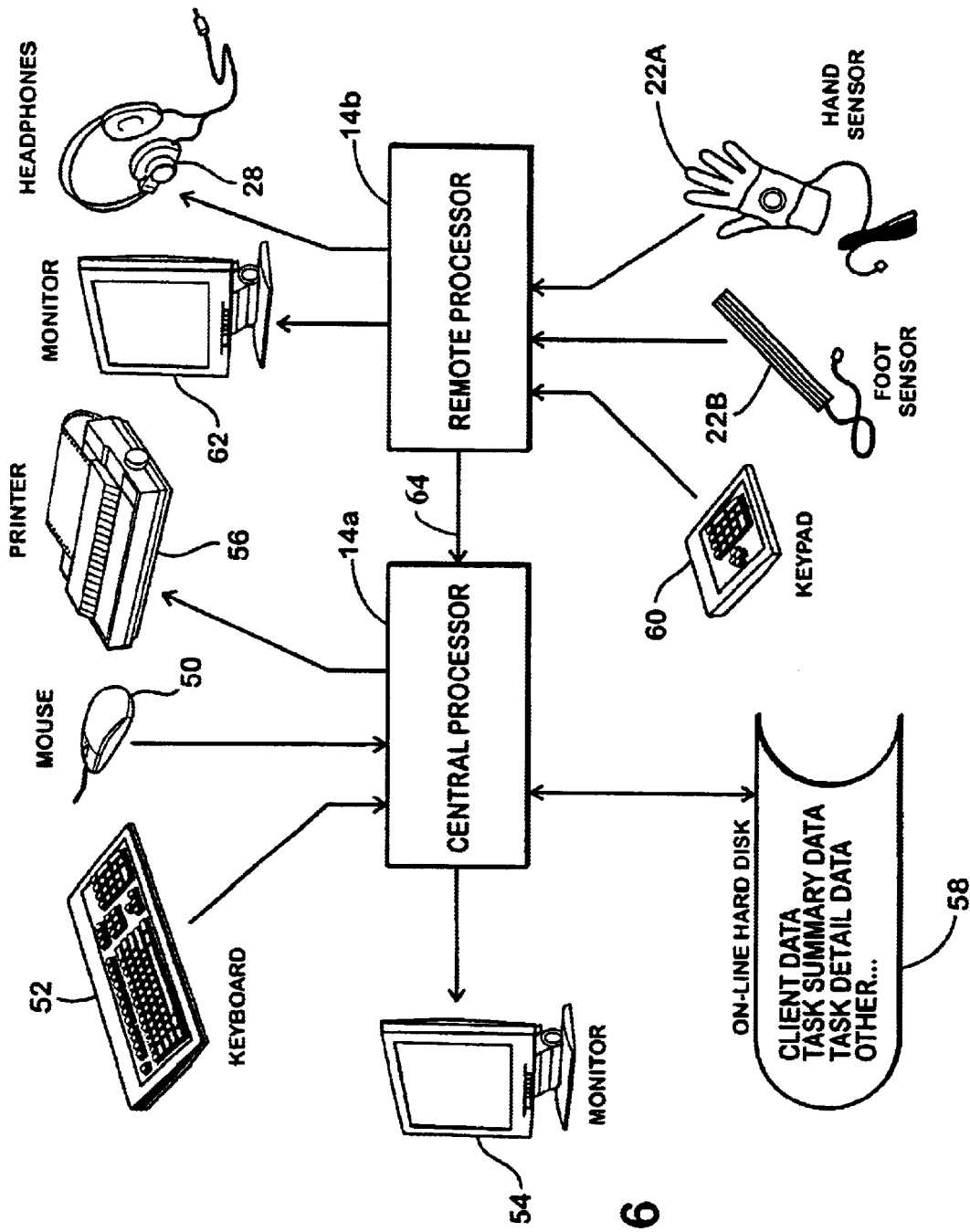
FIG. 6 is the same view as FIG. 4 of another alternative embodiment.

A more detailed illustration of computer system 20 is illustrated in FIG. 4. In addition to a processor 14, computer system 20 includes a mouse 50, keyboard 52, monitor 54 and printer 56. A hard drive 58 may contain the information in database 30, such as client data, task summary data, task detail data, and other data.

An alternative computer system 20 includes a central processor 14a and a remote processor 14b. The central processor 14a may be dedicated to program administration, task management, data management, time sequence generation, and the like. Remote processor 14b may manage the input and output functions for the triggers 22a, 22b and user interface headphones 28. Remote processor 14b may also be responsible for generating the reference signals, distraction signals, guidance signals, and the like, provided to the user.

In another alternative embodiment, a computer system 20" includes a central processor 14a' and a remote processor 14b'. In addition to handling the input/output for triggers and headphones, remote processor 14b may include a keypad 60 and display 62. In this manner, remote processor 14b', keypad 60, and display 62 may be combined into a compact, portable device capable of being carried by the user, such as being attached to the user's belt, or the like, while the user wears headphones 28 and operates the triggers 22a and/or 22b. Remote processor 14b may be connectable with central processor 14a' through a communication link 64 which may be a remote link, such as an infrared link, a radio frequency link, such as the Blue Tooth system marketed by Motorola Company, or other known remote link. In computer system 20", central processor 14a' may be utilized to make changes to remote processor 14b software and to process data generated at remote processor 14b'. Otherwise, remote processor 14b may be operable in a standalone fashion.

Figure 7:
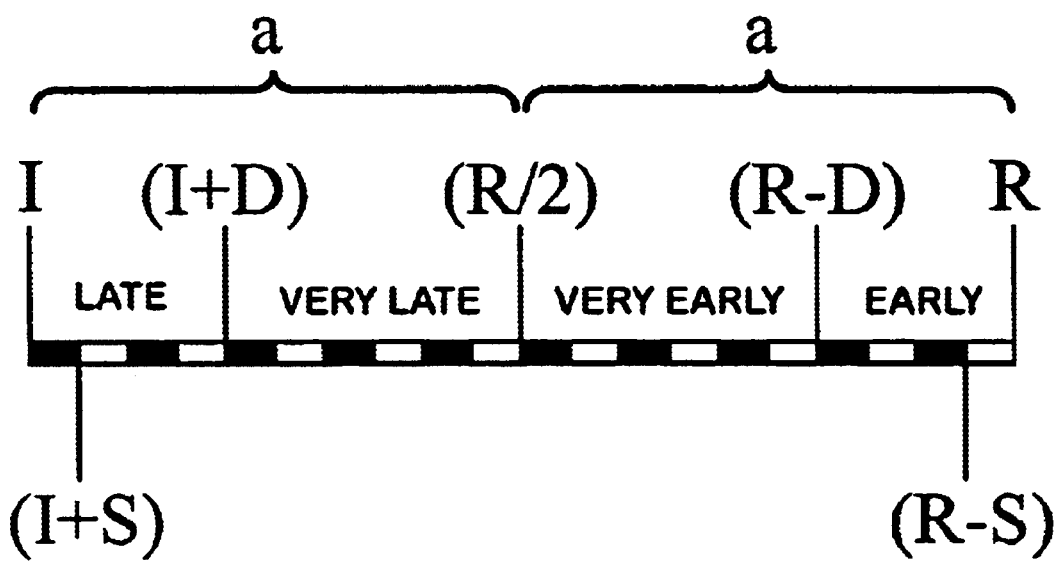
FIG. 7 is a diagram illustrating timing sequences for use with responses with respect to reference signals.

An illustration of timing assessment carried out by time assessment apparatus 12 is illustrated in FIG. 7. Referring to FIG. 7, the parameter 1 refers to the time that a reference signal is generated. The parameter R is an indication of the time at which another reference signal is generated. If a user's response occurs during interval "a," the response is late with respect to the reference signal occurring at I. If the user's response occurs during interval "b," the response is early with respect to the reference signal at R. The time intervals illustrated in FIG. 7 would be repeated for each sequence between occurrences of reference signals.

If the user responds in the period of I+S with respect to reference signal I, or in the period R–S with respect to reference signal R, the user response is deemed to be within the super difficulty range. This is considered a very accurate response. This may also be referred to as the "super right-on" range. If the user responds within the period of I+D, then the response is late with respect to reference signal I but within a difficulty range D. If a user responds within the range R–D, the response is deemed early with respect to reference signal R within the difficulty range D. If the user responds in the interval between I+D and R/2, the user response is deemed very late with respect to reference signal I. If the user response is in the range of R/2 to R–D, the response is deemed very early with respect to reference signal R.

Figure 8:
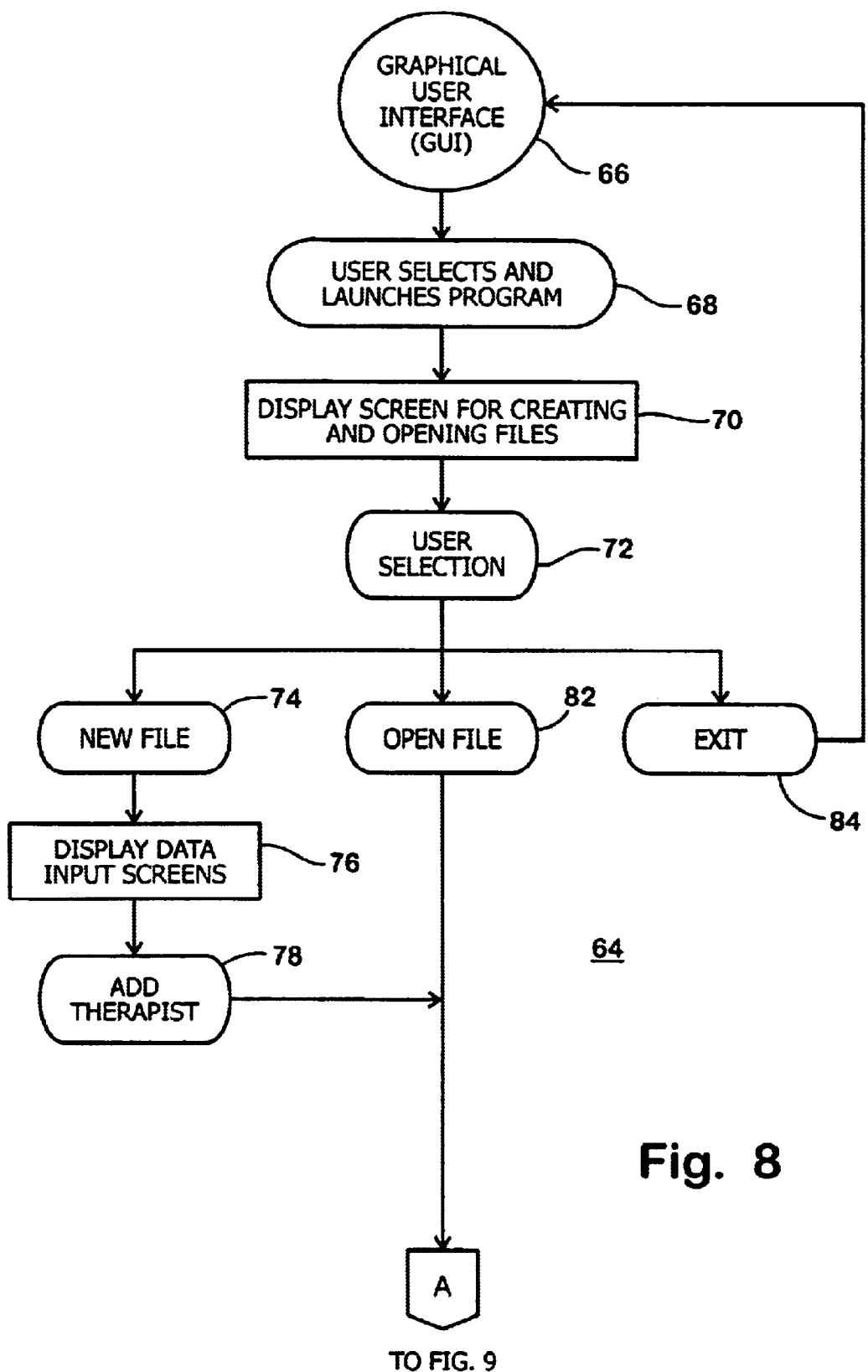
FIG. 8 is a flowchart of a data creation and input function.

A program 64 carried out by timing assessment tool 12 begins with a data creation and input function including a graphical user interface 66 displayed on monitor 54 from which the user selects and launches a program at 68 (FIG. 8). A screen, or menu, for creating and opening files is displayed on monitor 54 at 70 and the user is prompted to select a function to perform at 72. If the user selects a new file at 74, the monitor displays data input screens at 76 such as those illustrated in Appendix A attached hereto. The program then provides for identifying the therapist at 78. If the user selects at 72 to open an existing file at 82, the file is opened and the screen for choosing a mode is displayed at 80. If the user selects to exit the program at 72, the program is exited at 84 and returned to the graphic user interface at 66.

Figure 9:
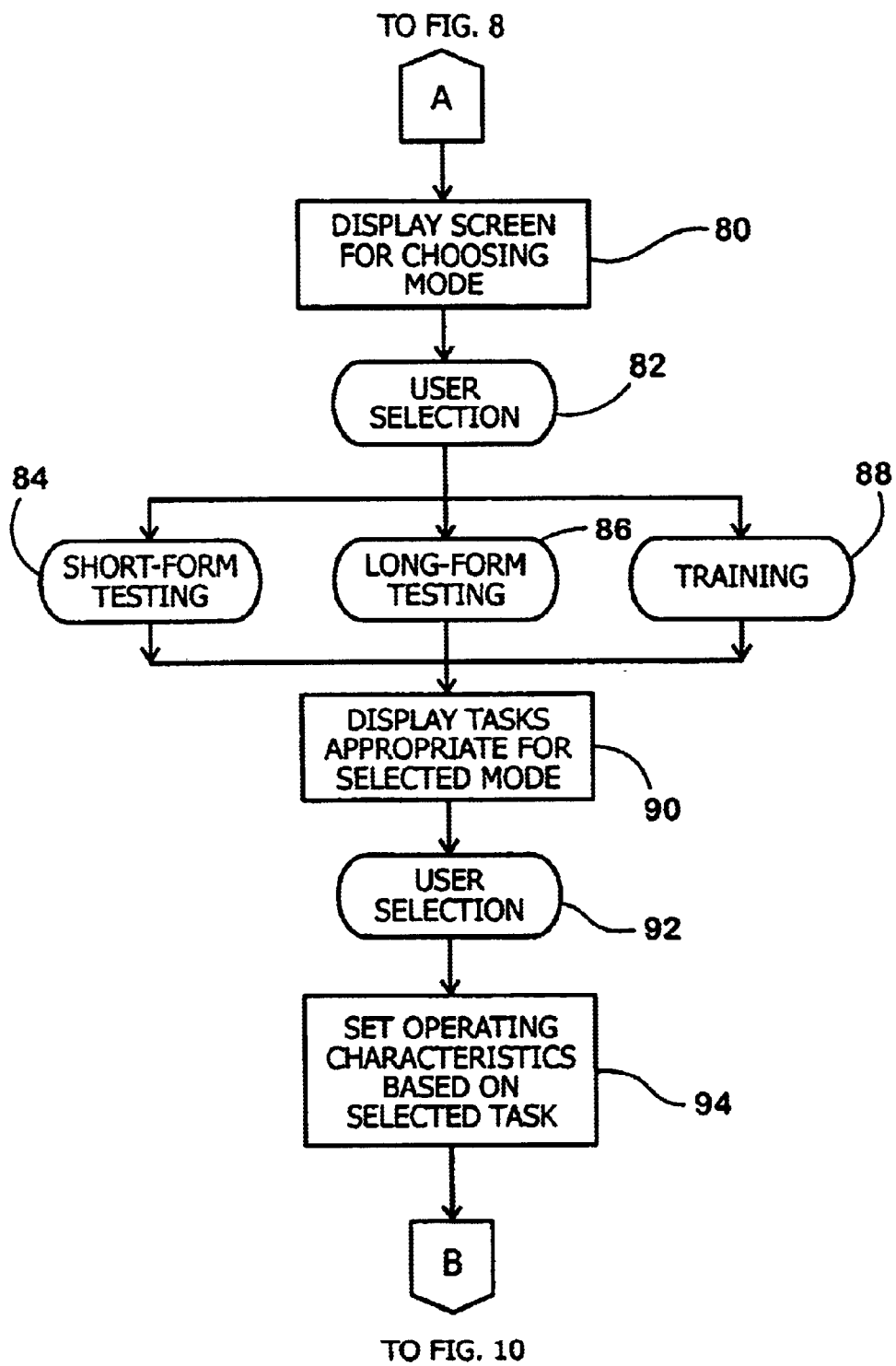
FIG. 9 is a flowchart of a mode and task selection function.

The program then proceeds to a mode and task selection function in which a screen is displayed at 80 for choosing a mode (FIG. 9). When the screen is displayed for choosing a mode at 80, the user makes a selection 82 from among a short-form testing routine 84, a long-form testing routine 86, and a training routine 88. The long-form testing mode 86 is illustrated in Appendix A. The short-form testing mode 84 provides a quick diagnostic input tool with lower test/retest accuracy. It includes a subset of the tests performed in the long-form testing mode, such as clapping both hands without guide sounds and clapping both hands with guide sounds. This shows auditory hypersensitivity when the user performs worse when the guide sounds are present. The short-form test may also be used to track user's session progress. In such case, the short-form test is performed at the beginning and end of each session. The long form is a series of preferably 14 to 16 tasks that are all performed preferably without guidance signals. The long form is preferably used when no rhythmicity training is anticipated or prior to and after rhythmicity training. The long-form testing mode can be used to measure the effectiveness of other physical and cognitive intervention not related to rhythmicity training. In both the short-form testing mode and the long-form testing mode, only reference signals may be presented to the user without the guidance signals. If the rhythmicity training mode 88 is selected, the user is presented with both reference sounds and guidance signals, or guidance signals alone, while the user is instructed to carry out various manipulations of hand sensor 22a and/or foot sensor 24b preferably under the guidance of a trained instructor or therapist. After the mode is selected at 82, the appropriate tasks are displayed on monitor 54 at 90 and operating characteristics may be selected by the user at 92 based upon the selected task at 94.

Figure 10:
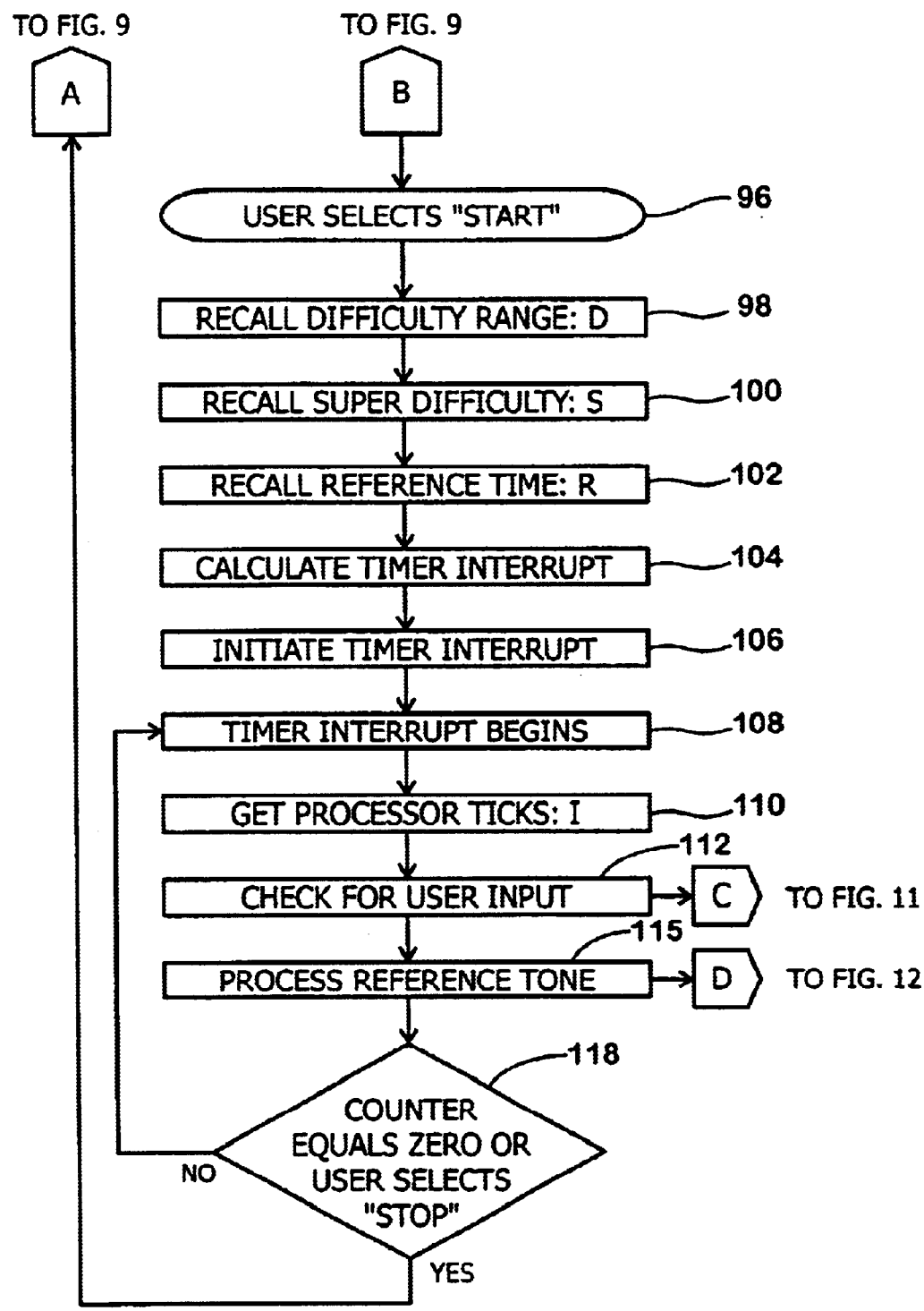
FIG. 10 is a flowchart of a timing interrupt processing function.
Figure 11:
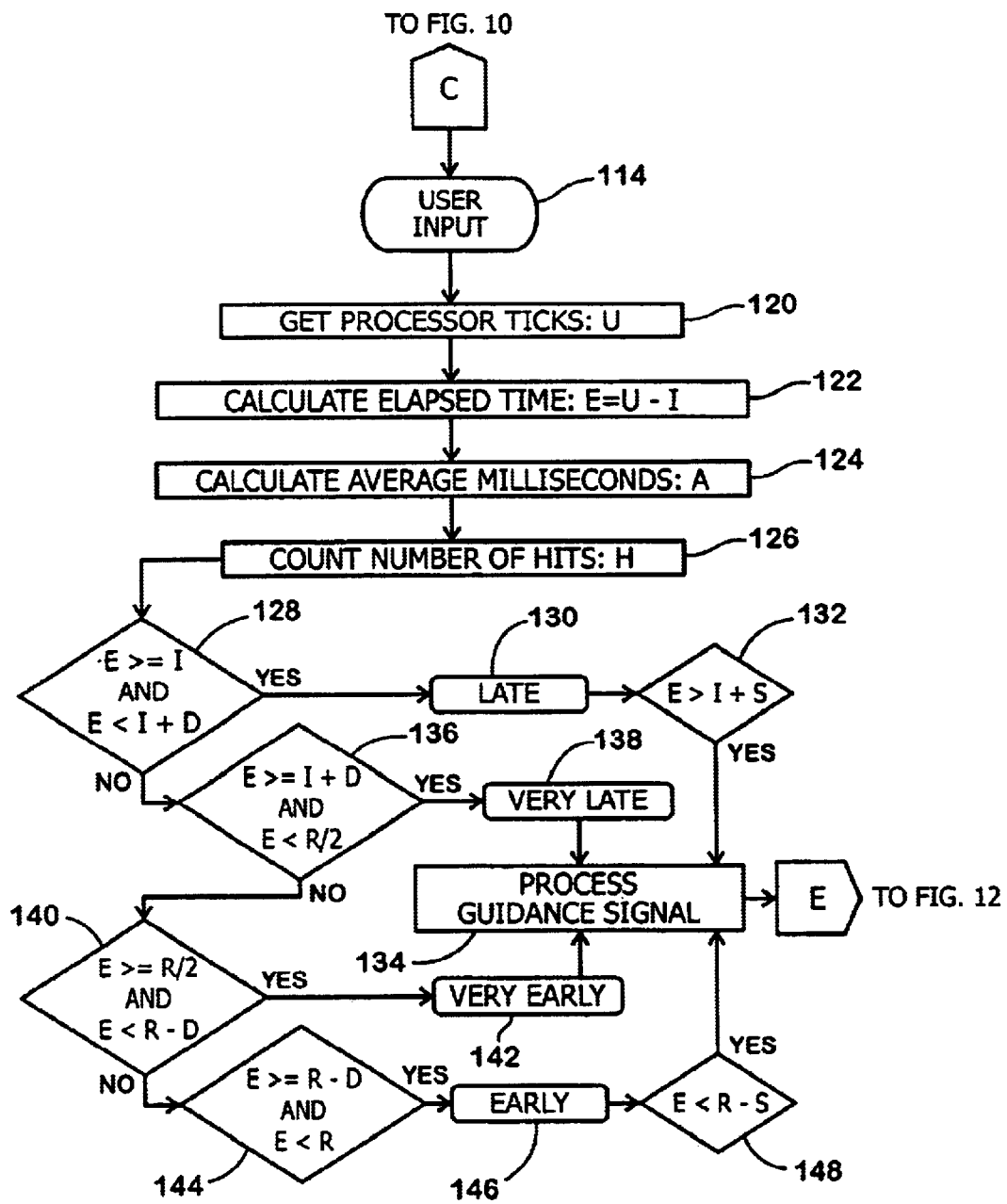
FIG. 11 is a flowchart of a temporal evaluation function.
Figure 12:
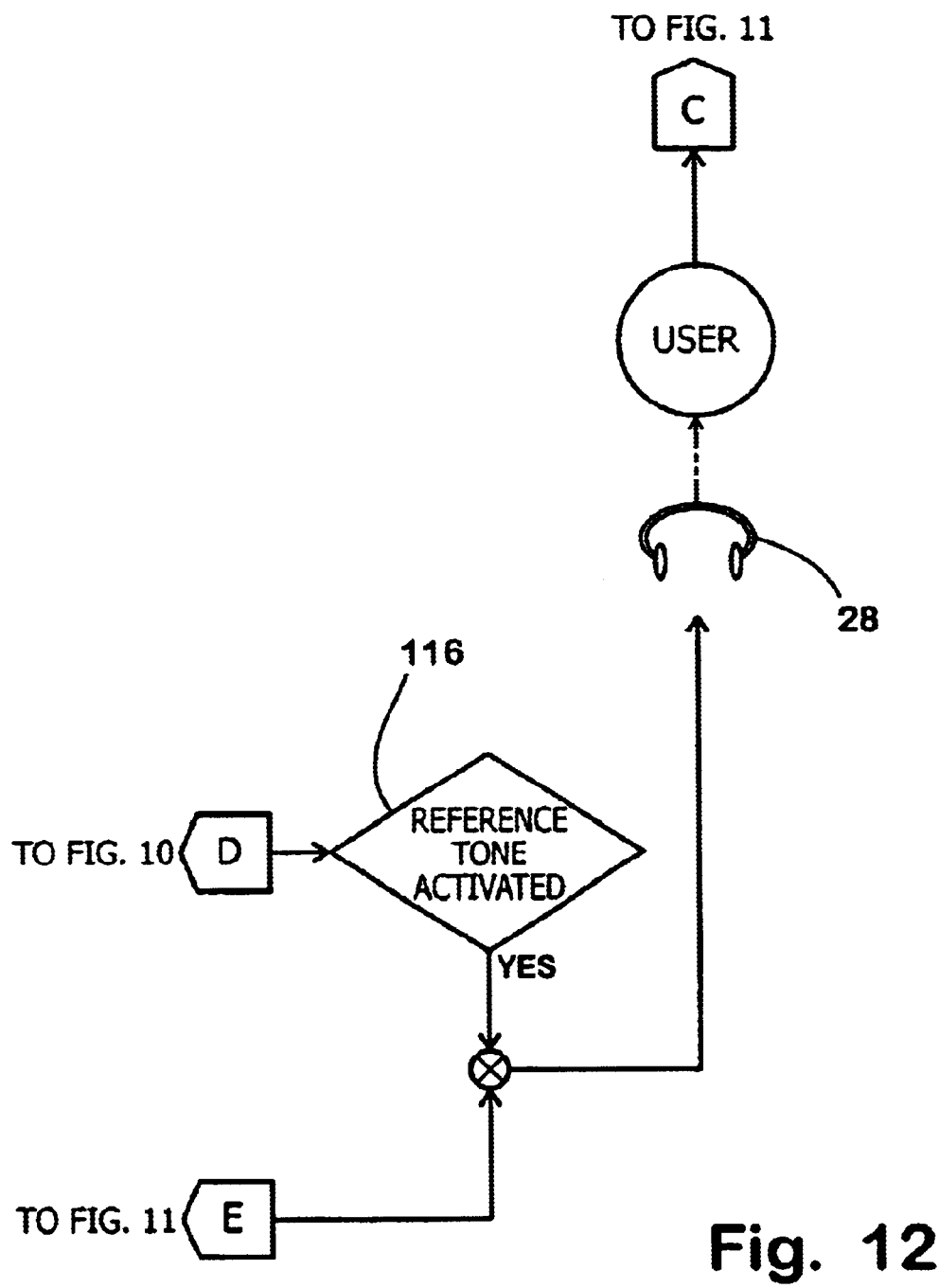
FIG. 12 is a flowchart of a user signal generation function.

Program 64 then performs a timing interrupt processing function (FIG. 10). When the user, or trainer, selects a "start" function at 96, computer 20, 20', 20" recalls parameters D, S and R from memory at 98, 100, 102 and calculates the value of I based upon the recalled parameters at 104. At 106, 108, the timer interrupt is initiated and the program begins at I (110). The program then checks for a user actuation of a trigger (22a, 22b) at 112. If a user input is received at 112, the user input is processed at 114 (FIG. 11). If a user response is not received at 112, the program determines at 115 whether it is time to generate a reference signal. If it is determined at 115 that it is time to generate a reference signal, then the program proceeds to FIG. 12 where it is determined at 116 whether the reference signal (ON/OFF) is activated. If the reference signal function is activated at 116, then a reference signal is generated, such as with headphones 28, and supplied to the user.

It is then determined at 118 whether a counter has decremented to zero or the trainer selects a "stop" function. The counter is set at the beginning of each mode and typically has a length that is a function of the mode selected. If the counter has not equaled zero, the program proceeds to 108 where another tick is processed at 110 and the program checks for user inputs (112) and processes references tones (115). When it is determined at 118 that the counter equals zero or the trainer selects the "stop" function, the program returns to the mode choosing display screen (80).

A temporal evaluation function is carried out at FIG. 11. When a user input is received at 114, the program reads the value of the processor ticks (U) at 120 and calculates an elapsed time parameter (E=U−I) at 122. At 124, a parameter A is updated. A is the average response, maintained in milliseconds, of the user with respect to the reference signal. The value of A may be displayed on monitor 54 for the purpose of monitoring by the therapist and recording in database 44. Although the use of an average response is illustrated, the database may store every response by the user in milliseconds early or milliseconds late. A parameter H is updated at 126. H is the number of user inputs conducted during the particular test.

It is then determined at 128 whether the value of E is greater than or equal to 1 and less than I+D. If so, it is determined at 130 that a late response has been received. It is then determined at 132 whether the parameter E is greater than I+S. If so, a guidance signal is generated at 134 and supplied to headphones 28 if the particular mode calls for the presentation of guidance signals to the user. Preferably, guidance signals are generated during an optional training mode 88, but not generated during long-form testing mode 86 or one of the tasks of short-form testing mode 84. If it is determined at 132 that the value of E is not less than I+S, a late response within the super difficulty range was received. Preferably, no guidance signal is generated for a response falling within the super difficulty range, even if the particular mode calls for the presentation of guidance signals to the user. Preferably, the super difficulty range is from 15 milliseconds before occurrence of the reference signal to 15 milliseconds after. However, it could extend to as low as between 5 milliseconds before and after occurrence of the reference signal. This provides an indication to the user, who would hear only the reference signal and no guide signal, that the user has produced a response in the super difficulty range.

If the requirements of 128 are not met, it is determined at 136 whether E is greater than I+D and less than R/2. If so, the user response is determined to be very late at 138 and an appropriate guidance signal is generated at 134 if the particular mode calls for the generation of guidance signals. If the condition of 136 is not met, it is determined at 140 whether E is greater than R/2 and less than R−D. If so, it is determined that a very early response is received at 142 and an appropriate guidance tone will be generated at 134 if guidance tones are being generated. If the condition at 140 is not met, it is determined at 144 whether E is greater than R−D and less than R. If so, it is determined at 146 that an early response has been received and it is determined at 148 whether the response is prior to the super difficulty range. If so, an appropriate guidance tone is generated at 134 if guidance tones are being generated. If it is determined at 148 that E is between R−S and R, no guidance tone is generated even if guidance tones are being generated. This is an indication to the user that the user's response is within the super difficulty range.

Thus, it is seen that the present invention provides an objective tool which provides the therapist with the ability to establish a diagnosis and/or corrective intervention for a child long before the neurological conflicts blossom into full learning disabilities. In this manner, the self-esteem and academic performance of the child can progress normally without the one or four lost years which are common with conventional diagnostic procedures. Furthermore, a diagnostic technique, according to the invention, significantly reduces administrator reliance on empirical observations and reduces subjective error potential.

Unlike known testing machines, which test for one, and only one, conflict, such as ADHD, the present invention provides the ability to distinguish among different conflicts. Furthermore, the present invention operates on subconscious awareness, rather than the known diagnostic system which operates on conscious awareness. Because the present invention utilizes rhythmic reference sounds, it is enjoyable to use. It also does not tend to easily generate frustration in the user, unlike known systems which easily frustrate users, especially ones most prone to the conflict being tested.

The present invention also provides a diagnostic tool which utilizes the same general technique used for improving performance in the same underlying neurological conflict that is being diagnosed. Thus, after a diagnosis is made, an intervention may be prescribed using the same timing instrument.

The present invention measures a fundamental parameter of the user that operates at an underlying level of the neurological system. In particular, the invention measures habits, which prevent users from optimally using the fundamental planning and sequencing mechanisms within their brains which control the natural timing patterns of their actions and thoughts. The invention may also be used to measure user's distractibility, such as their ability to ignore internal thoughts and external stimuli which interfere with their ability to stay on task. Distractibility may also include the ability to focus attention on a single stimulus or task over both short and long periods without being interrupted by internal thoughts or external stimuli.

Changes and modifications in the specifically described embodiments can be carried out without departing from the principles of the invention which is intended to be limited only by the scope of the appended claims, as interpreted according to the principles of patent law including the doctrine of equivalents.

---

APPENDIX A

---

TEST DATA SHEET (CONFIDENTIAL)

---

A) PATIENT SURVEY

1) Individual Client Demographics

ID Number/Name Connection (Assigned by program)

Testing Center Name/Code

Name of clinic: _____
Test administrator name: _____
Date of Testing: mm/dd/yyyy
Time of Testing: _____ am/pm

APPENDIX A-continued

TEST DATA SHEET (CONFIDENTIAL)

Diagnostic codes

Please indicate the professionally confirmed diagnosis(es) of this client:

| Diagnosis — DSMIV/ ICD-9-CM Code | Primary Diagnosis | Secondary Diagnosis | Tertiary Diagnosis |
|---|---|---|---|
| Autism Spectrum | | | |
| 01. Autistic Disorder 299.0 | | | |
| 02. Asberger — 299.80 | | | |
| 03. Pervasive Dev Dis — 299.80 | | | |
| ADHD | | | |
| 04. Combined — 314.01 | | | |
| 05. Predominately Hyperactive-Impulsive Type — 314.01 | | | |
| 06. Predominately Inattentive Type — 314.00 | | | |
| 07. Cerebral Palsy — 343.9 | | | |
| 08. Downs — 758.0 | | | |
| 09. Parkinson's — 332.0 (ICD) | | | |
| Traumatic Brain Injury (TBI) | | | |
| 10. Post Accident — 294.1 | | | |
| 11. Organic Mental Syndrome due to trauma — 291.1 | | | |

Professional verification code

Name of professional making medical diagnosis:
Last Name: _____, First Name: _____ Initial: _____
Professional Background:

1. Psychiatrist
2. Clinical Psychologist
3. Pediatrician
4. Developmental or Behavioral Pediatrician
5. Pediatric Neurologist
6. Physical Medicine (Rehabilitation)
7. Other qualified diagnostician Professional Classification of Therapist 1. Occupational Therapist
2. Speech Pathologist
3. Physical Therapist
4. Educator
5. Other Professional Gender: Male, Female
Birth date: mm/dd/yyyy
Body Weight: _____ pounds

| Medication Information: | Dosage | Times/Day | Hours since last taken |
|---|---|---|---|
| 1. Stimulant (e.g., Ritalin, Dexedrine, Adderall) | | | |
| 2. SSRI (e.g., Prozac, Luvox, Zoloft) | | | |
| 3. Non-SSRI anti-depressants (e.g., Imipramine (Tofranil), Wellbutrin) | | | |
| 4. Major tranquilizer (e.g., Risperidal, Zyprexa) | | | |
| 5. Minor tranquilizer (e.g., Valium) | | | |
| 6. Anti-seizure (e.g., Depakote) | | | |
| 7. Mood stabilizer (e.g., Lithium, Depakote) | | | |
| 8. Other medical condition medication | | | |

Handedness:

Self reported:

Handedness: 1. Right 2. Left   By what means determined?: _____
Footedness: 1. Right 2. Left   By what means determined? _____

APPENDIX A-continued

TEST DATA SHEET (CONFIDENTIAL)

Clinically Verified:

Handedness:    1. Right 2. Left    By what means determined?: _____
    Footedness:    1. Right 2. Left    By what means determined? _____

Suggested Clinical Verified Test:

Handedness:    Present a ball or other object to client at vertical midline of body. Observe which hand is used. Do three times and accept the hand used 2 or 3 times within the three trials.
    Footedness:    Place ball on floor in front of client at vertical midline of the body. Ask client to walk or run toward the ball and softly kick the ball. Repeat three times and accept the foot used 2 or 3 times within the three trials.

2) Parent/Guardian Provided Information

Parental/Guardian Approval

All parents/guardians are asked to sign this release form at the time of IM Long form testing.
I understand that it would be helpful to study the effect of the Interactive Metronome in influencing timing as it relates to planning and sequencing. I therefore agree to the release of all testing and IM interaction data and information of my son/daughter/ward. I also understand my son/daughter/ward's name will not be provided with the information nor will his/her individual information be made public or identified with his/her name.

Name of Dependent: _____
Name of Parent Guardian: _____
Signature of Parent/Guardian:
Date: _____

Highest level of parent(s) education

1. Less than high school graduation
2. High school graduate\GED
3. Some college/post secondary education
4. College graduate
5. Graduate school education Family income level:

1. Under $15,000 per year
2. 15,000–$19,999 per year
3. $20,000–$29,999 per year
4. $30,000–$39,999 per year
5. $40,000–$49,999 per year
6. $50,000–$75,000 per year
7. Over $75,000

Sports and Music Experience

Please indicate which of the following activities the client has participated in within the two year?

| | | | |
|---|---|---|---|
| 1. | Organized team sports such as football, hockey, basketball, etc | 1. No | 2. Yes |
| 2. | Organized Individual sports such as tennis, golf, running, etc | 1. No | 2. Yes |
| 3. | Other organized sports | 1. No | 2. Yes |
| 4. | Plays a musical instrument/takes music lessons | 1. No | 2. Yes |
| 5. | Organized dance training/performance | 1. No | 2. Yes |

Remedial program participation

Indicate if the client participates in any of the following types of programs:

| | | | |
|---|---|---|---|
| 1. | Speech and language remediation | 1. No | 2. Yes |
| 2. | Title 1 or other remedial reading program(s) | 1. No | 2. Yes |
| 3. | Learning disability program(s) | 1. No | 2. Yes |

3) Clinical Assessment by Therapist

Please provide the following information about this client. If you do not feel able to answer a specific question, just leave it blank.

Vision:

1. Severe visual deficit
2. Glasses, aided/corrected vision to near normal
3. Normal, no corrective lens Hearing:

1. Totally deaf
2. Impaired one ear, Right
3. Impaired one ear, Left
4. Impaired both ears
5. Normal hearing General health:

1. Poor
2. Fair

APPENDIX A-continued

TEST DATA SHEET (CONFIDENTIAL)

3. Good
4. Excellent

|  | Superior To Age | Age Appropriate | Mild | Moderate Compromised | Severe |
|---|---|---|---|---|---|
| Processing Capacity Profile | | | | | |
| 1. Motor planning and sequencing: | | | | | |
| Gross motor | 5 | 4 | 3 | 2 | 1 |
| Fine motor | 5 | 4 | 3 | 2 | 1 |
| Activity level | 5 | 4 | 3 | 2 | 1 |
| Muscle tone | 5 | 4 | 3 | 2 | 1 |
| 2. Balancing Capabilities | 5 | 4 | 3 | 2 | 1 |
| 3. Visual/spatial processing (Search for hidden objects, sense of direction, etc) | 5 | 4 | 3 | 2 | 1 |
| 4. Auditory processing (Ability to remember multiple step directions, etc.) | 5 | 4 | 3 | 2 | 1 |
| 5. Sensory modulation (General tendency toward sensory, hypo or hyper reactivity) | | | | | |
| Tactile (touch) | | | | | |
| Hypoactivity | 5 | 4 | 3 | 2 | 1 |
| Hyperactivity | 5 | 4 | 3 | 2 | 1 |
| Sound | | | | | |
| Hypoactivity | 5 | 4 | 3 | 2 | 1 |
| Hyperactivity | 5 | 4 | 3 | 2 | 1 |
| Pain | | | | | |
| Hypoactivity | 5 | 4 | 3 | 2 | 1 |
| Hyperactivity | 5 | 4 | 3 | 2 | 1 |
| Movement | | | | | |
| Hypoactivity | 5 | 4 | 3 | 2 | 1 |
| Hyperactivity | 5 | 4 | 3 | 2 | 1 |
| Space | | | | | |
| Hypoactivity | 5 | 4 | 3 | 2 | 1 |
| Hyperactivity | 5 | 4 | 3 | 2 | 1 |
| Functional Developmental Capacities | | | | | |
| Please assess the client's functional capacities for each of the following: | | | | | |
| 1. To focus and attend | 5 | 4 | 3 | 2 | 1 |
| 2. To engage with others with trust and Intimacy | 5 | 4 | 3 | 2 | 1 |
| 3. To be intentional and/or purposeful with Motor and/or other gestures | 5 | 4 | 3 | 2 | 1 |
| 4. To engage in multi-step problem solving interactions with others | 5 | 4 | 3 | 2 | 1 |
| 5. To use ideas to express intentions, wishes and feelings | 5 | 4 | 3 | 2 | 1 |
| 6. To use imagination | 5 | 4 | 3 | 2 | 1 |
| 7. To use ideas logically in an interpersonal context | 5 | 4 | 3 | 2 | 1 |
| 8. To use ideas logically in an academic context. | 5 | 4 | 3 | 2 | 1 |

B) TIMING ASSESSMENT

1) Test Sequence

Interactive Metronome Long Form Measurements

Individual tapping sequences:      Millisecond (MS) Scores (+/−)      Absolute Millisecond (MS) Scores
1. Both hands
2. Right hand
3. Left hand
4. Alternating both toes
5. Right toe
6. Left toe
7. Alternating both heels
8. Right heel
9. Left heel
10. Right hand/Left toe

APPENDIX A-continued

TEST DATA SHEET (CONFIDENTIAL)

11. Left hand/Right Toe
12. Balance Right Foot/Left Toe
13. Balance Left Foot/Tap Right Toe
14. Both hands with guide sounds
    Totals (1–14)

|  | Means | Mean MS | Mean Absolute |
|---|---|---|---|
|  | Stand Dev | SD MS | SD Abs |
|  | Counts | N | N |

2) Test Evaluation

Tapping averages:

Mean of Tasks 1 through 14 = Sum of task means (1–14)/14
IM Long Form Test Battery
    Calculations:
        a. Hands mean
            a1. = 1 + 2 + 3 + 14/4 Hand/Guide sound mean
            a2. = 1 + 2 + 3/3 Hand Mean
        b. Foot and upper/lower limb mean average = (Add items 4 through 13)/10
        c. Add a2 + b = _____
            Unadjusted test average = c/2
        d. Auditory hypersensitivity mean = (a1 + b)/2
Burst Counts/IARs:

Percent hits within ±15 ms. Formula: (n of hits within ±15 ms/Assigned Task Hits) × 100
Highest number of hits in a row (IAR) within ±15 ms and the number of times occurring.
E.g., 6 hits in a row/2 times (High IAR/N)
Next highest IAR and the number of times occurring.
Planning and Sequencing Patterns Disassociative:  No definite pattern of hits. Performance involves skipped hits and multiple hits
                between beats.
                1. Missed Hits:
                    (Number of Missed Hits between beats/Assigned Task Hits) × 100
                2. Extra Hits:
                    (Number of extra hits above 1 between beats/Assigned Task Hits) × 100
                3. Standard deviation of all hits. Used to measure central tendency and
                    "randomness" of hits. Same as Directional MS hits standard deviation.
♦ * ♦ * * ♦ * ♦ * * * ♦ ♦ * ♦
Contraphasic:  How close are hits to the 555 ms scale center.
                Definition: Mean, standard deviation and number of all hits between −277 ms
                    to +277 ms
Hyperballistic:  Trainer and/or Trigger may be used to measure ballistic motions of the patient
                operating the triggers.
                Compute means and standard deviations.
                  A. Trainer measures:
                    Trainer will observe hyperballistic movements (hardness of hits and length
                    of time hands are together and then assign a 1–9 index number.
                    Definition elements: Limb movements lack smooth control. Movements
                    are snappy, quick, or jerky (ballistic) in nature and lack continuous motion.
                    1. No hyperballistic behavior: Very smooth, coordinated movements
                        with no sign of ballistic motions.
                      .
                      .
                      .
                    5. Moderate amount of hyperballistic behavior
                      .
                      .
                      .
                    9. Extreme amounts of hyperballistic behavior. Constant ballistic limb
                        movements throughout the task with no sign of continuous, smooth
                        coordinated motions.
                B. Trigger measures:
                  Pressure measure:
                    Compute the mean and standard deviation of the pressure level of all
                    hits
                  Trigger contact time:
                    Compute the mean and standard deviation of the contact time duration
                    of all hits
                Measure launch speed of movements.
Hypoanticipatory:  Mean, standard deviation and number of hits that fall in the
                0 to +555 ms interval.
Hyperanticipatory  Mean, standard deviation and number of hits that fall in the
                −555 to 0 ms interval.
Auditory Hypersensitivity:  Develop a randomized sound presentation with no guide sounds to
                      assess impact of sounds on performance. Measure this by calculating
                      the above five Planning and Sequencing Patterns indices.

APPENDIX A-continued

TEST DATA SHEET (CONFIDENTIAL)

The Second/Milli-second Time Line

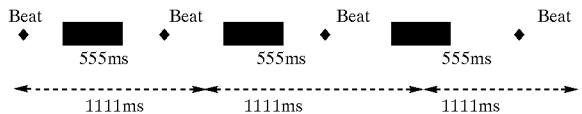

Therapist notes and observations:

---

The embodiments of the invention in which an exclusive property or privilege is claimed are defined as follows:

1. A neurological conflict diagnostic apparatus, comprising
   a timing assessment tool manipulatable by a user in response to the user's expected occurrence of a rhythmic reference signal;
   said timing assessment tool deriving a rhythmic assessment from a pattern of user responses to the user's expected occurrence of the rhythmic reference signal; and
   an analyzer responsive to said rhythmic assessment to indicate a diagnosis or a corrective intervention.

2. The diagnostic apparatus in claim 1 wherein said rhythmic reference signal comprises a percussive tone having occurrences separated by a substantially constant time interval.

3. The diagnostic apparatus in claim 2 wherein said timing assessment tool provides said rhythmic reference signal to the user.

4. The diagnostic apparatus in claim 3 wherein said rhythmic reference signal is at least one of a non-speech tone and a speech phonetic sound.

5. The diagnostic apparatus in claim 2 wherein said timing assessment tool supplies distraction sounds to the user.

6. The diagnostic apparatus in claim 1 wherein said analyzer includes a database, said database relating rhythmic assessment and diagnosis or corrective interventions, and wherein said analyzer further includes a processor applying said rhythmic assessment to said database and retrieving a diagnosis or a corrective intervention from said database.

7. The diagnostic apparatus in claim 6 wherein said processor retrieves a corrective intervention from said database.

8. The diagnostic apparatus in claim 7 wherein the corrective intervention includes at least one chosen from neurological time sequence training, a school-based intervention, and a pharmacological intervention.

9. The diagnostic apparatus in claim 6 wherein said database is developed from rhythmic assessments for a multiplicity of users and diagnosis for the multiplicity of users.

10. The diagnostic apparatus in claim 9 wherein said rhythmic assessments for said multiplicity of users are developed with said timing assessment tool.

11. The diagnostic apparatus in claim 9 wherein said diagnosis includes an indication of a level of accuracy of the diagnosis.

12. The diagnostic apparatus in claim 6 wherein said processor retrieves a diagnosis from said database.

13. The diagnostic apparatus in claim 12 wherein said diagnosis is selected from among at least Attention Deficit Hyperactivity Disorder (ADHD), Oppositional Defiant Disorder (ODD), Dyslexia, NVLD, tics, such as Tourette Syndrome (TS), Closet Head Injury (CHI), language disorder, Developmental Coordination Disorder (DCD), Deficit and Attention Motor Control and Perception (DAMP), Language Impaired (LI), Aggressive-Hyperactive-Impulsive-Inattentive behavior (AHII), autism, Parkinson's disease, and claustrophobia.

14. The diagnostic apparatus in claim 6 wherein said processor retrieves both a diagnosis and an intervention from said database.

15. The diagnostic apparatus in claim 1 wherein said timing assessment tool includes at least one user operable trigger and a control, said control generating said reference signal and determining a temporal relationship between user manipulation of said at least one trigger and occurrences of said reference signal.

16. The diagnostic apparatus in claim 15 wherein said at least one user operable trigger includes a plurality of triggers operable by different user limbs.

17. The diagnostic apparatus in claim 16 wherein said timing assessment tool compares user manipulation of different said triggers.

18. The diagnostic apparatus in claim 16 wherein said plurality of triggers are operable by the user's hands and feet.

19. The diagnostic apparatus in claim 15 wherein said control provides to the user a guidance signal that is a function of said temporal relationship.

20. The diagnostic apparatus in claim 19 wherein said guidance signal is one of an aural signal and a visual signal.

21. The diagnostic apparatus in claim 19 wherein said guidance signal is an aural signal.

22. The diagnostic apparatus in claim 15 wherein said pattern of user responses is chosen from at least one of user response time, user response variability, break in user response sequence, out-of-phase user response, erratic user responses, user responses before the reference signal, user responses after the reference signal and multiple responses.

23. The diagnostic apparatus in claim 1 wherein the rhythmic assessment is one of disassociative, contraphasic, hyperballistic, hypoanticipatory, hypermiticipatory or auditory hypersensitivity.

24. The diagnostic apparatus in claim 1 wherein said pattern of user manipulations of said timing assessment tool is chosen of at least one of response time, response variability, break in response sequence, out-of-phase responses, erratic responses, early responses, late responses and multiple responses.

25. A diagnostic apparatus, comprising:
   at least one user operative trigger;
   a control generating a reference signal having occurrences separated by predetermined time intervals, said control measuring a temporal relationship between user manipulation of said trigger and occurrences of said reference signal and determining a pattern of the temporal relationships; and a database comprising a plurality of said patterns of temporal relationships and diagnosis or corrective interventions relating to the temporal relationships;

wherein said control applies the pattern of temporal relationships to said database.

26. The diagnostic apparatus in claim 25 wherein said control measures said temporal relationship for user manipulation of different said triggers.

27. The diagnostic apparatus in claim 26 wherein said plurality of triggers are operable by the user's hands and feet.

28. The diagnostic apparatus in claim 25 wherein said control provides to the user a guidance signal th is a function of said temporal relationship.

29. The diagnostic apparatus in claim 28 wherein said guidance signal is one of an aural signal and a visual signal.

30. The diagnostic apparatus in claim 29 wherein said guidance signal is an aural signal.

31. The diagnostic apparatus in claim 25 wherein said control provides said reference signal to the user.

32. The diagnostic apparatus in claim 31 wherein said reference signal is at least one of a non-speech tone and a speech phonetic sound.

33. The diagnostic apparatus in claim 25 wherein said patterns of temporal relationships are made up of at least one chosen from user response time, user response variability, break in user response sequence, out-of-phase user responses, erratic user responses, user responses before the reference signal, user responses after the reference signal and multiple responses each reference signal.

34. The diagnostic apparatus in claim 25 wherein said patterns of temporal relationships comprise one chosen from disassociative, contraphasic, hyperballistic, hypoanticipatory, hyperanticipatory or auditory hypersensitivity.

35. The diagnostic apparatus of claim 25 wherein said database comprises corrective interventions for the patterns of temporal relationships, wherein the corrective interventions include at least one of training programs with said at least one user operable trigger and said control, a school-based intervention, and a pharmacological intervention.

36. The diagnostic apparatus of claim 25 wherein said database is developed from said patterns of temporal relationships for a multiplicity of users and diagnosis for said multiplicity of users.

37. The diagnostic apparatus in claim 36 wherein said patterns of temporal relationships for said multiplicity of users arc developed with at least one said user operable trigger and a said control.

38. The diagnostic apparatus in claim 36 wherein said patterns of temporal relationships for said multiplicity of users are developed with said timing assessment tool.

39. The diagnostic apparatus in claim 36 including applying statistical analysis to the pattern of temporal relationships of the multiplicity of users and the diagnosis for the multiplicity of users.

40. The diagnostic apparatus in claim 25 wherein said database comprises diagnosis related to the temporal relationships.

41. The diagnosis apparatus in claim 40 wherein said diagnosis includes an indication of a level of accuracy of the diagnosis in the database.

42. The diagnosis apparatus in claim 40 wherein said diagnosis is selected from among at least Attention Deficit Hyperactivity Disorder (ADHD), Oppositional Defiant Disorder (ODD), Dyslexia, NVLD, tics, such as Tourette Syndrome (TS), Closed Head Injury (CHI), language disorder, Developmental Coordination Disorder (DCD), Deficit and Attention Motor Control and Pereeption (DAMP), Language Impaired (LI), Aggressive-Hyperactive-Impulsive-Inattentive behavior (AHII), autism, Parkinson's disease, and claustrophobia.

43. The diagnosis apparatus in claim 25 wherein said database comprises a plurality of temporal relationships and both diagnosis and corrective interventions relating to the temporal relationships.

44. The diagnosis apparatus in claim 25 wherein said control also generates distraction sounds.

45. A method of determining a diagnosis or a corrective intervention for a person having a neurological conflict, comprising:

providing a database of rhythmic assessments and diagnosis or corrective interventions;

measuring a pattern of user responses to expected occurrences of a rhythmic reference signal and determining a rhythmic assessment for that user from the pattern of user responses oft that user; and applying the rhythmic assessment of that user to the database and retrieving a diagnosis or a corrective intervention from said database.

46. The method of determining a therapeutic intervention or corrective intervention of claim 45 wherein said rhythmic reference signal comprises a percussive tone having occurrences separated by a substantially constant time interval.

47. The method of determining a therapeutic intervention or corrective intervention of claim 45 wherein said measuring includes providing a timing assessment tool and having the user manipulate the timing assessment toot to develop the pattern of user responses of that user.

48. The method of determining a therapeutic intervention or corrective intervention of claim 47 wherein said timing assessment tool includes at least one user operable trigger and a control generating said reference signal and determining a temporal relationship between user manipulation of said at least one trigger and occurrences of said reference signal.

49. The method of determining a therapeutic intervention or corrective intervention of claim 48 wherein said at least one user operable trigger includes a plurality of triggers operable by different user limbs.

50. The method of determining a therapeutic intervention or corrective intervention of claim 49 including manipulating said plurality of triggers by different limbs of the person to determine said rhythmicity.

51. The method of determining a therapeutic intervention or corrective intervention of claim 48 including providing the reference signal to the user.

52. The method of determining a therapeutic intervention or corrective intervention of claim 48 including providing a distraction signal to the user.

53. The method of determining a therapeutic intervention or corrective intervention of claim 47 wherein said pattern of user responses includes at least one chosen from the user's response time, response variability, break in response sequence, out-of-phase responses, erratic responses, early responses, and late responses.

54. The method of determining a therapeutic intervention or corrective intervention of claim 45 wherein said pattern of user responses includes at least one chosen from the user's response time, response variability, break in response sequence, out-of-phase responses, erratic responses, early responses, late responses and multiple responses.

55. The method of determining a therapeutic intervention or corrective intervention of claim 45 wherein said rhythmic assessment is chosen from one of disassociative, contraphasic, hyperballistic, hypoanticipatory, hyperanticipatory or auditory hypersensitivity.

56. The method of determining a therapeutic intervention or corrective intervention of claim 45 including applying the rhythmic assessment to the database and retrieving a corrective intervention from said database, wherein said corrective intervention comprisesis chosen from at least one of a neurological time sequence training, a school-based intervention and a pharmacological intervention.

57. The method of determining a therapeutic intervention or corrective intervention of claim 45 including developing the database by determining a rhythmic assessment of a multiplicity of persons and recording the rhythmic assessment and a diagnosis for the multiplicity of users.

58. The method of determining a therapeutic intervention or corrective intervention of claim 57 including determining the rhythmic assessment of said multiplicity of persons with at least one user operable trigger and generating a reference signal, the reference signal having occurrences separated by a predetermined time interval and determining a temporal relationship between user manipulation of said at least one trigger and occurrences of said reference signal.

59. The method of determining a therapeutic intervention or corrective intervention of claim 57 wherein said developing the database includes recording an indication of a level of accuracy of the diagnosis.

60. The method of determining a therapeutic intervention or corrective intervention of claim 45 including applying the determined rhythmic assessment to the database and retrieving a diagnosis from the database.

61. The method of determining a therapeutic intervention or corrective intervention of claim 60 including retrieving diagnosis from among at least Attention Deficit Hyperactivity Disorder (ADHD), Oppositional Defiant Disorder (ODD), Dyslexia, NVLD, tics, such as Tourette Syndrome (TS), Closed Head Injury (CHI), language disorder, Developmental Coordination Disorder (DCD), Deficit and Attention Motor Control and Perception (DAMP), Language Impaired (LI), Aggressive-Hyperactive-Impulsive-Inattentive behavior (AHII), autism, Parkinson's disease, and claustrophobia.

62. The method of determining a therapeutic intervention or corrective intervention of claim 45 including applying the determined rhythmic assessment to the database and retrieving a diagnosis and a corrective intervention from the database.

* * * * *

UNITED STATES PATENT AND TRADEMARK OFFICE
CERTIFICATE OF CORRECTION

PATENT NO. : 6,719,690 B1
APPLICATION NO. : 10/048505
DATED : April 13, 2004
INVENTOR(S) : James F. Cassily It is certified that error appears in the above-identified patent and that said Letters Patent is hereby corrected as shown below:

Column 1:
Line 6-7, "provisional patent application Serial" should be --International Patent Cooperation Treaty Application Ser.--
Line 7, Insert --PCT/US00/21855 filed on August 11, 2000, which claims priority from provisional application Ser. No.-- after "No."
Line 32, "." should be --,-- after "(ODD)"
Line 39, "Psychiatrv" should be --Psychiatry--

Column 3:
Line 56, Insert --neuralgic-- after "a"

Column 4:
Line 39, Insert --20-- after "computer"

Column 5:
Line 14, "I" should be --l-- (lower case L)

Column 7:
Line 25, "14b" should be --14b'--
Line 31, "14b" should be --14b'--
Line 39, "14b" should be --14b'--
Line 42, "1" should be --I-- (the number one)

Column 9:
Line 17, "1" should be --I-- (the number one)

Column 13:
Family Income Level:, Insert --$-- before "15,000"

Column 20:
Line 16, Claim 13, "Closet" should be --Closed--
Line 55, Claim 23, "hypermiticipatory" should be --hyperanticipatory--

Column 21:
Line 16, Claim 28, "th" should be --that--
Line 33, Claim 33, Insert --for-- after "responses"
Line 51, Claim 37, "arc" should be --are--

UNITED STATES PATENT AND TRADEMARK OFFICE
CERTIFICATE OF CORRECTION

PATENT NO. : 6,719,690 B1
APPLICATION NO. : 10/048505
DATED : April 13, 2004
INVENTOR(S) : James F. Cassily It is certified that error appears in the above-identified patent and that said Letters Patent is hereby corrected as shown below:

Column 22:
Line 5, Claim 42, "Pereeption" should be --Perception--
Line 23, Claim 45, "oft" should be --of--
Line 34, Claim 47, "toot" should be --tool--

Column 23:
Line 10, Claim 56, Delete --comprises--

Signed and Sealed this

Eighteenth Day of July, 2006

JON W. DUDAS
*Director of the United States Patent and Trademark Office*